United States Patent
Kraft et al.

(10) Patent No.: US 9,199,903 B2
(45) Date of Patent: Dec. 1, 2015

(54) METHOD FOR THE PURPOSE OF A CATALYTIC CONDENSATION OR COUPLING

(71) Applicant: Fraunhofer Gesellschaft zur Förderung der angewandten Forschung e.V., München (DE)

(72) Inventors: Axel Kraft, Oer-Erkenschwick (DE); Andreas Menne, Mülheim an der Ruhr (DE); Klaas Breitkreuz, Bochum (DE); Thoralf Gross, Brunsbüttel (DE); Holger Ziehe, Itzehoe (DE)

(73) Assignees: FRAUNHOFER GESELLSCHAFT ZUR FÖRDERUNG DER ANGEWANDTEN FORSCHUNG E.V., München (DE); SASOL GmbH, Hamburg (DE)

( * ) Notice: Subject to any disclaimer, the term of this patent is extended or adjusted under 35 U.S.C. 154(b) by 0 days.

(21) Appl. No.: 14/364,422

(22) PCT Filed: Dec. 13, 2012

(86) PCT No.: PCT/EP2012/005152
§ 371 (c)(1),
(2) Date: Jun. 11, 2014

(87) PCT Pub. No.: WO2013/087211
PCT Pub. Date: Jun. 20, 2013

(65) Prior Publication Data
US 2014/0343325 A1 Nov. 20, 2014

(30) Foreign Application Priority Data

Dec. 14, 2011 (DE) .......................... 10 2011 120 923
Dec. 15, 2011 (DE) .......................... 10 2011 121 087

(51) Int. Cl.
*C07C 45/45* (2006.01)
*C07C 45/71* (2006.01)
*C07C 29/34* (2006.01)
*C10L 1/02* (2006.01)

(52) U.S. Cl.
CPC ................. *C07C 45/45* (2013.01); *C07C 29/34* (2013.01); *C07C 45/71* (2013.01); *C10L 1/02* (2013.01)

(58) Field of Classification Search
CPC .......... C07C 29/34; C07C 45/45; C07C 45/71
USPC ........................................................ 568/391
See application file for complete search history.

(56) References Cited

FOREIGN PATENT DOCUMENTS

EP 0299720 A2 * 1/1989 ............ C07C 31/125

OTHER PUBLICATIONS

Olson et al. Higher-Alcohol Biorefinery—Improvement of Catalyst for Ethanol Conversion. Applied Biochemistry and Biotechnology, 2004, vol. 113-116, 913-932.*
Bruno et al. Comparison of Biomass-Derived Turbine Fuels with the Composition-Explicit Distillation Curve Method. Energy & Fuels, 2011, vol. 25, 1847-1858.*

* cited by examiner

*Primary Examiner* — Sikarl Witherspoon
(74) *Attorney, Agent, or Firm* — Edward E. Sowers; Brannon Sowers and Cracraft PC

(57) ABSTRACT

The invention relates to a method for catalytically condensing organic compounds containing at least one oxo and/or hydroxyl function into CH acidic compounds and/or coupling said organic compounds to the CH acidic compounds in the presence of a catalyst which comprises an active carbon substrate provided with a metal. The method is suitable in particular for generating higher alcohols, aldehydes, ketones, and/or alkanes as well as mixtures thereof.

20 Claims, 1 Drawing Sheet

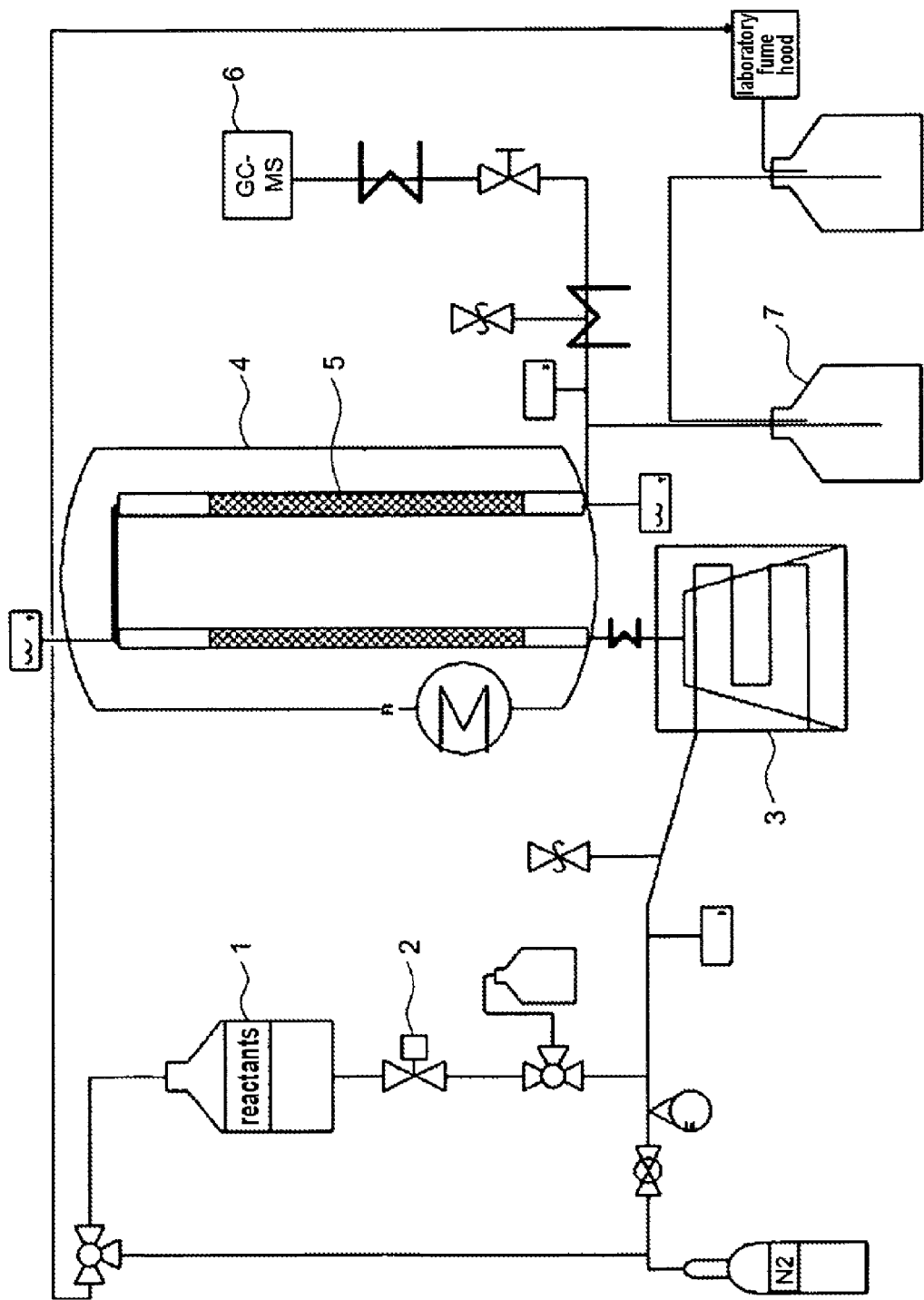

METHOD FOR THE PURPOSE OF A CATALYTIC CONDENSATION OR COUPLING

CROSS-REFERENCES TO RELATED APPLICATIONS

This application is a National Stage filing of International Application PCT/EP 2012/005152, filed Dec. 13, 2012, claiming priority to German applications DE 10 2011 120 923.2 filed Dec. 14, 2011, and DE 10 2011 121 087.7 filed Dec. 15, 2011, entitled "METHOD FOR THE PURPOSE OF A CATALYTIC CONDENSATION OR COUPLING." The subject application claims priority to PCT/EP 2012/005152, to DE 10 2011 120 923.2, and to DE 10 2011 121 087.7 and incorporates all by reference herein, in their entirety.

BACKGROUND OF THE INVENTION

The present invention relates to the technical field of catalytic condensation or coupling of alcohols or carbonyl compounds with CH-acidic compounds, in particular for producing higher alcohols, aldehydes, ketones, aromatics and/or alkanes and also mixtures thereof.

In particular, the present invention relates to a method for the catalytic condensation or coupling of organic compounds containing oxo and/or hydroxyl functions with CH-acidic compounds.

In addition, the present invention relates to products and product mixtures, in particular alcohols, aldehydes, ketones, alkanes and/or aromatics, and also mixtures thereof, which are obtainable by the method according to the invention.

Furthermore, the present invention relates to the use of the products or product mixtures according to the invention as combustibles or transport fuels and also as chemicals for private and industrial purposes.

Finally, the present invention relates to the use of an activated carbon substrate provided with at least one metal as catalyst for the catalytic condensation or coupling of organic compounds containing oxo and/or hydroxyl functions with CH-acidic compounds.

A central problem of chemical-industrial production is the synthesis of longer-chain nonpolymeric compounds starting from short-chain, inexpensive and also industrially available starting materials for the purpose of producing high-value chemical products, such as, for example, surfactants, additives, or else certain combustible fractions. In this connection, in particular, higher-molecular-weight alcohols are of importance.

One possibility of generating, for example, high-molecular-weight alcohols, is what is termed the Guerbet reaction, in which primary or secondary alcohols are coupled, in particular in a basic environment, and mostly branched primary alcohols are obtained.

In the reaction named after the chemist Marcel Guerbet, in the actual meaning it is an organic reaction in which primary or secondary alcohols are reacted catalytically with elimination of one equivalent of water to form beta-alkylated dimerized alcohols, wherein, usually, hydrogenation catalysts known per se such as, for example, what is termed Raney nickel, or alkali metal hydroxides or alkali metal alkoxides are used.

The production of what are termed these Guerbet alcohols proceeds from the prior art usually in a homogeneous catalytic process in which principally alkali metal and alkaline earth metal catalysts in the form of their hydroxides are used, which must then be separated off after the synthesis and thus generate waste. In the process, the synthesis proceeds under elevated pressure and at temperatures which are usually below the boiling point of the starting materials, which very greatly restricts the flexibility of the method for low-boiling alcohols (cf. DE 693 16 349 T2, EP 0 299 720 A2, U.S. Pat. No. 766,677 A, US 2010/0298613 A1, WO 91/04242 A1 and WO 2011/054483 A1).

From these higher alcohols, in subsequent reaction steps, further products such as, for example alkanes, can be produced. In particular, it is in addition possible in complex processes to obtain alkane mixtures having comparable properties to aviation gasoline, in particular kerosene.

On account of the enormous demand for aircraft kerosene, what is termed JET-A1 or Jetfuel, of about 200 million tonnes worldwide—in Germany alone, over 8.5 million tonnes were consumed in 2010—for provision of the required alkanes on a biogenic basis, the conversion of a widely available, favorable and regenerative raw material is necessary. Also, in particular against the background of increasing trade with $CO_2$ certificates, the production of a sustainable biokerosene or admixture thereof to fossil-produced kerosene is of very great interest to the aviation industry.

Usually, the paraffins used as aviation fuels are obtained in the form of what is termed a middle distillate of crude oil refining and consist, inter alia, of approximately 35% by mass of branched and unbranched $C_8$-$C_{15}$ alkanes.

Known processes, for producing kerosene on the basis of renewable raw materials are principally based on the hydrogenation or hydrotreating of vegetable oils. However, principally unbranched and saturated alkanes form, the boiling point and freezing point range of which differs markedly from fossil-based kerosene. Therefore, additional isomerization and hydrocracking steps are necessary.

To date there still does not exist a method to produce kerosene by direct catalytic condensation from alcohols, in particular not on the basis of renewable raw materials.

In addition, higher alcohols, in particular branched alcohols (what are termed Guerbet alcohols) and linear alcohols, and also alkanes and alkenes in the boiling range of Jetfuel cannot yet be produced by a one-step heterogeneously catalyzed condensation without hydrogen from, in particular, bio-based shorter-chain alcohols. Therefore, dehydration, for example, to form alkenes and oligomerization of the alkenes must be provided upstream, in order in this manner to build up the required carbon chain. In order to generate kerosene, hydrogenation must be carried out afterward, or producing alcohols, hydration must be performed again (cf. in particular EP 0 099 690 A2).

According to the prior art, higher alcohols can equally be produced by aldol condensation, wherein homogeneous catalysts, such as inorganic hydroxides, or similarly strong bases, are used. However, this route has not been usable economically to date for kerosene production.

The multistage production of bio-based kerosene is also possible from bio-based furfurals or derivatives and ketones thereof, such as, e.g., acetone. The furfurals required for this purpose must however first be obtained from lignocellulose in a complex manner.

In further methods for producing kerosene according to the prior art, in part oxygen-containing compounds are used in such a manner that the resultant products likewise do not conform to the valid standard for kerosene or aviation fuels, in particular jet fuel. Such a method is described, for example, in EP 1 218 472 A1.

In addition, the production of aviation gasoline via dehydration of isobutanol and other alcohols produced by fermentation, in particular what are termed fusel alcohols, and the following oligomerization of the resultant alkenes with subsequent hydrogenation is known, such as, for example, as described in the IATA 2010 Report on Alternative Fuels (December 2010), Ref. No.: 9709-03, ISBN 978-92-9233-491-8.

Since the condensation in particular of alcohols and aldehydes to give higher alcohols, alkanes etc. and optionally the further reaction thereof, at least in theory, promises an accessible route to higher molecular compounds, in the prior there has been no lack of attempts to improve the existing condensation methods or develop novel methods on this basis.

CA 2 298 545 A1 relates to a method for producing metal-free Guerbet alcohols, wherein primary or secondary alcohols are condensed in the presence of alkaline catalysts or heavy metal catalysts at high temperatures with removal of the resultant water.

DE-A 29 12 068 relates to a method for producing hydrocarbons in which alcohols are reacted by means of transition metal or heavy metal catalysts. In the method described, principally olefins, and also to a lesser extent, aromatics, are obtained as products.

In addition, EP 1 052 234 A1 relates to a method for producing starting materials or raw materials for the chemical industry, and also high-octane motor fuels by catalytic reaction of ethanol by means of a calcium phosphate catalyst which contains an activating metal.

The scientific publication "*Synthesis of Biogasoline from Ethanol over Hydroxyapatite Catalysts*", T. Tsuchida, T. Yoshioka, S. Sakuma, T. Takeguchi and W. Ueda, Ind. Eng. Chem. Res. 47, pages 1443 to 1452 (2008) relates to the production of bio-based motor fuels from ethanol.

In addition, the scientific publication "*Integration of C—C coupling reactions of biomass-derived oxygenates to fuel-grade compounds*", E. I. Gürbüz, E. L. Kunkes and J. A. Dumesic, Applied Catalysis B: Environmental 94, pages 134 to 141 (2010) relates to the reaction of oxygenated organic compounds obtained from biological processes to produce motor fuels.

Similarly, the scientific publication "*Conversion of biomass-derived butanal into gasoline-range branched hydrocarbon over Pd-supported catalysts*", S. M. Kim, M. E. Lee, J.-W. Choi, D. J. Suh and Y.-W. Suh, Catalysis Communications 16, pages 108 to 113 (2011) relates to the reaction of butanal obtained by biosynthesis to form motor fuels.

Furthermore, the scientific publication "*Combined solid base/hydrogenation catalysts for industrial condensation reactions*", F. King and G. J. Kelly, Catalysis Today 73, pages 75 to 81 (2002), relates to catalysts for industrially employed condensation reactions.

The scientific publication "*Reactions of methanol and higher alcohols over H-ZSM-5*", A. C. Gujar, V. K. Guda, M. Nolan, Q. Yan, H. Toghiani and M. G. White, Applied Catalysis A: General 363, pages 115 to 121 (2009), relates to condensation reactions of methanol and higher alcohols.

Finally, the scientific publication "*Hydrotalcide-derived mixed oxides as catalyst for different C—C bond formation reactions from bioorganic materials*", S. Ordóñez, E. Díaz, M. León and L. Faba, Catalysis Today, Vol. 167, pages 71 to 76 (2011), firstly describes the self-condensation of acetone and also the self-condensation of ethanol in each case in the gas phase, and secondly describes the aldol condensation of furfuryl alcohol with acetone in the liquid phase. The condensation reactions of acetone or ethanol in the gas phase can only be carried out in greatly diluted gas streams and deliver extremely low conversion rates. Also, the liquid phase reaction of furfuryl alcohol and acetone can only be carried out with extremely low reactant concentrations and requires at least 24 hours of reaction time in order to achieve conversion rates of approximately 70%, wherein the product selectivity is extremely low.

The above-described methods are therefore not suitable for synthesizing chemical compounds, in particular not on an industrial scale.

The above-described methods of the prior art all have the disadvantage that condensation reactions of alcohols and carbonyl compounds only proceed in low yields, in particular only in low space-time yields, or only with low space velocities, and so these methods are of low efficiency and cannot be carried out in a worthwhile manner economically.

In addition, in the methods of the prior art, a process procedure is required which is complex to implement, with dilution of the reactants with inert gas or solvents, such as water, for example. Most of the above-described methods of the prior art in addition use catalyst systems having catalyst service lives which are inadequate under large-scale conditions. Also, it is frequently difficult to provide controllable reaction conditions, in such a manner that yields and product mixtures cannot be obtained in a reliable manner. Most of the methods described are therefore unsuitable for large-scale applications.

BRIEF SUMMARY OF THE INVENTION

The object of the present invention is therefore to provide a method which permits an efficient condensation or coupling of organic compounds even under industrial conditions and which at least substantially avoids or else at least decreases or weakens the above-described disadvantages of the prior art.

In particular, an object of the present invention is considered to be to provide a method which is suitable in particular for generating higher alcohols, aldehydes, ketones, aromatics and/or alkanes, and also mixtures thereof, and in particular can also be carried out under industrial or large-scale application conditions.

To achieve the above-described object, the present invention proposes a method described herein.

The present invention further relates to the products or product mixtures that are obtainable by the method according to the invention.

Again the present invention further relates to the use of the products or product mixtures according to the invention.

Finally, the present invention still further relates to the use of an activated carbon substrate as catalyst as described herein.

Of course, designs, embodiments, advantages or the like which are described hereinafter only with reference to one aspect of the invention—for purposes of avoiding unnecessary repetition—obviously apply correspondingly in relation to the remaining aspects of the invention.

In addition, obviously, in the details hereinafter of values, numbers and ranges, the respective values, numbers and range details are not to be understood as limiting; obviously, to a person skilled in the art, it is possible to deviate from the stated ranges or details on account of individual cases or of an application-specific manner, without departing from the context of the present invention.

In all of the relative or percentage, in particular weight-related indications of quantity cited hereinafter, in addition, it must be noted that they are selected in the context of the present invention by a person skilled in the art in such a manner that, in total—optionally with incorporation of further components or ingredients or additives, in particular such as defined hereinafter—always result in 100%. This is obvious to a person skilled in the art, however.

In addition, all of the details of values or parameters cited hereinafter, or the like, can be detected or determined in principle with standardized or explicitly stated methods of determination or methods of determination familiar to an expert in this field.

With this proviso, the present invention is described in more detail hereinafter.

BRIEF DESCRIPTION OF THE DRAWINGS

FIG. 1 provides a schematic depiction of the experimental setup used herein.

DETAILED DESCRIPTION OF THE INVENTION

The present invention—according to a first aspect of the present invention—therefore relates to a method for the catalytic condensation and/or coupling of organic compounds containing at least one oxo and/or hydroxyl function with CH-acidic compounds, using which, in particular higher alcohols, aldehydes, ketones, aromatics and/or alkanes, and also mixtures thereof can be generated.

The method according to the invention is carried out in such a manner that
(A) at least one organic compound containing at least one oxo and/or hydroxyl function and which has at least 3 carbon atoms and is selected from the group of primary and/or secondary alcohols, aldehydes and ketones and also mixtures thereof,
is reacted with
(B) with at least one CH-acidic compound, which preferably has at least 3 carbon atoms,
in the presence of at least one catalyst, wherein the catalyst comprises an activated carbon substrate that is provided, in particular is doped, with at least one metal.

The method according to the invention is outstandingly suitable for producing higher alcohols, aldehydes, ketones, aromatics and/or alkanes and also mixtures thereof in high yields and with high selectivity. This is all the more surprising, as, for the process procedure according to the invention, the use of a catalyst based on activated carbon is sufficient, which is loaded or impregnated with at least one metal.

In addition, using the process described, by condensation of two or more linear or branched alcohols or aldehydes, in particular also higher, branched in particular in the beta position, alcohols—what are termed Guerbet alcohols—and/or the corresponding aldehydes are formed.

Depending on the process conditions, the method according to the invention offers, in particular, the possibility for producing what are termed Guerbet alcohols in a fixed-bed reactor. The alkanes which are likewise formed as by-product can optionally be selectively separated off, in such a manner that a pure alcohol fraction can be obtained firstly, and a pure alkane fraction secondly, if desired (cf. e.g. U.S. Pat. No. 7,465,846 B2).

Surprisingly, the method according to the invention, however, can also be carried out in such a manner that a large fraction of the products occurs as hydrogenated Guerbet alcohols or the rearrangement products thereof, substantially alkanes and in small amounts alkenes. By adding water to the reaction mixture or to the reactants, the selectivity toward alkanes can be still further increased. Although the additional introduction of hydrogen during the coupling or condensation reaction is optional, it is not absolutely necessary for the proceeding hydrogenation processes.

It was likewise not predictable that also low-boiling alcohols such as, for example, n-propanol, n-butanol, n-pentanol or n-hexanol, optionally without the application of pressure, can be reacted to form higher alcohols, in particular Guerbet alcohols, and optionally—in particular without further purification—can be reacted to form motor fuels, such as gasoline or kerosene.

It has proved to be particularly advantageous in this case that the method according to the invention can be carried out continuously. This is not possible in the classic Guerbet alcohol synthesis which is operated discontinuously or batchwise, and so the products thereof, just from the economic aspect alone, cannot be used as motor fuels or as reactants for the synthesis of motor fuels.

The mixture of various hydrocarbons forming in the method according to the invention offers the possibility of direct admixture to fossil kerosene, without modifying the physical properties, in particular the freezing points, and without having to perform a prior isomerization, as must be carried out, for example, when hydrogenated vegetable oils are used.

A further advantage of the method according to the invention in comparison with the familiar homogeneously catalyzed Guerbet alcohol syntheses is, in addition, that, firstly, no aqueous salt-containing waste due to the neutralization of highly concentrated basic catalysts such as, for example, potassium hydroxide solution, is formed, and that, secondly, there is no risk of corrosion when usual reactors which are fabricated from stainless industrial steel (e.g. steel material 1.4571 or AISI 316 Ti) are used.

To date, there exists no comparable heterogeneously catalyzed method for producing kerosene and Guerbet alcohols or generally higher alcohols, aldehydes, ketones, aromatics and/or alkanes, which is to be carried out in this manner simply and flexibly with respect to raw material selection and serves not only for production of valuable chemical production, but also for specific production of aviation gasoline, in particular kerosene.

Suitable catalysts for carrying out the method according to the invention consist, in particular, of shaped activated carbon which is basic, or provided with a basic finish, which, in particular, consists of a carbonaceous material which has been mixed with a binder and doping reagents and treated thermally with an activation gas, such as will be described further hereinafter. The catalytic activity results in particular from a combination of the properties of the carbonaceous support and the doping reagents.

Expensive heavy metal dopings are unnecessary for the method described of carbon chain extension of alcohols, but optionally, additional doping can also be used, if this should be desirable for reasons of selectivity, the reaction procedure or the process technology.

Furthermore, the additional use of hydrogen is optional. In each case, via the method according to the invention—compared with hydrogenation of fats and oils—hydrogen is saved.

The catalysts used have a high lifetime and water tolerance. Likewise, in the context of the present invention, the addition of an inert gas, in particular nitrogen, can be dispensed with.

The products or product mixtures obtained by the method according to the invention can be used in this case without further preparation, in particular without further reaction, as transport fuel or transport fuel additive for commercially conventional motor vehicle engines.

Via the targeted selection of the reactants or reactant mixtures, the product distribution or the resultant product mixture can be tailored to virtually any desired requirement profile.

In addition, the method according to the invention is also extremely flexible in the actual process procedure, and also in the selection of the usable reactants: for instance, the method according to the invention can be carried out, for example, unpressurized, that is to say at atmospheric pressure, or under pressure, and also in the gas phase or in the liquid phase, wherein in each case very good conversion rates and selectivities are achieved.

Equally, as reactants, not only pure substances or mixtures of pure substances can be used, but also fermentation products or fermentation by-products as are formed, for example, in the production of bioethanol, or else industrial waste products. By means of the method according to the invention, these by-products and waste products can also be fed back to creation of value and converted to valuable products or raw materials.

As already described above, in the context of the method according to the invention, as a reagent, an organic compound (A) containing at least one oxo and/or hydroxyl function is used, which preferably has at least 3 carbon atoms, and is selected from the group of primary and/or secondary alcohols, aldehydes and ketones (including hydroxyketones) and mixtures thereof.

In this case, in the context of the present invention, it can be provided that the organic compound (A) containing at least one oxo and/or hydroxyl function is selected from $C_3$-$C_{25}$ compounds, in particular $C_3$-$C_{20}$ compounds, preferably $C_3$-$C_{15}$ compounds, more preferably $C_3$-$C_{10}$ compounds, particularly preferably $C_3$-$C_8$ compounds, and also mixtures of various compounds having the abovementioned carbon number.

Equally, it can be provided that the organic compound (A) containing at least one oxo and/or hydroxyl function is selected from linear or branched compounds. In the context of the process procedure according to the invention, therefore, a broad spectrum of possible compounds (A) can be used, i.e. the method according to the invention can be carried out extremely flexibly and non-critically with respect to the choice of the organic compound (A) containing at least one oxo and/or hydroxyl function.

The expression "primary and/or secondary alcohol", in the context of the present invention, is taken to mean not only primary and secondary alcohols in the actual sense, but also diols and polyols, which have at least one primary and/or secondary alcohol group. In particular, the expression "primary and/or secondary alcohol", in the context of the present invention, also covers vicinal diols, in particular glycols, such as, for example, 1,2-propanediol, which, in the context of the present invention, is to be considered not only as a primary alcohol, but also as a secondary alcohol.

As described above, in the context of the method according to the invention, as second reactant, what is termed a CH-acidic compound (B) is used. In the context of the present invention, the expression "CH-acidic" is to be taken to mean, in particular, that a C—H bond, in particular in the presence of suitable bases, eliminates a proton and a negative charge remains on the carbon atom. In other words, CH acidity denotes, in particular, the tendency of an organochemical compound to release as protons hydrogen atoms bound to a carbon atom, and thus formally to act or function as an acid ("Brønsted acid" or proton donor).

Also, the CH-acidic compound (B) used in the context of the present invention as a further reactant can be selected from a multiplicity of possible compounds, in particular also from mixtures of different compounds.

It is preferred if the CH-acidic compound (B) has at least 3 carbon atoms. Generally, the CH-acidic compound (B) is selected from $C_3$-$C_{25}$ compounds, in particular $C_3$-$C_{20}$ compounds, preferably $C_3$-$C_{15}$ compounds, more preferably $C_3$-$C_{10}$ compounds, particularly preferably $C_3$-$C_8$ compounds, and also mixtures of various compounds having the abovementioned carbon number.

In addition, it can be provided that the CH-acidic compound (B) is selected from the group of primary and/or secondary alcohols, carboxylic acids, carboxylic anhydrides, carboxylic esters, aldehydes, ketones (including hydroxyketones), nitriles, nitro compounds, organic nitrates and mixtures thereof.

Particularly good results are obtained in the context of the present invention if the CH-acidic compound (B) is selected from the group of primary and/or secondary alcohols, carboxylic anhydrides, carboxylic esters, aldehydes, ketones (including hydroxyketones), nitriles, nitro compounds, organic nitrates and mixtures thereof, preferably from the group of primary and/or secondary alcohols, aldehydes, ketones, nitro compounds and mixtures thereof.

In particular, in the context of the present invention, particularly good results are obtained if preferably primary and/or secondary alcohols, aldehydes and ketones, in each case linear or branched, having a chain length of 4 to 8 carbon atoms and also mixtures thereof are used as CH-acidic compound (B).

Alternatively, the CH-acidic compound (B) can be selected from nitroalkanes, in particular nitromethane and/or nitroethane.

By using nitroalkanes, in particular by reacting nitromethane and/or nitroethane with alcohols, aldehydes and ketones, in particular $C_6$-$C_{10}$ nitroalkanes are accessible, which are added according to the prior art, in particular to commercially conventional diesel transport fuels as cetane number enhancers or as what are termed diesel boosters.

Particularly good results are achieved thereby in the context of the present invention if the method according to the invention is carried out in such a manner that (A) at least one organic compound containing at least one oxo and/or hydroxyl function and which has at least 3 carbon atoms and is selected from the group of primary and/or secondary alcohols, aldehydes and ketones and also mixtures thereof, is reacted with (B) with at least one CH-acidic compound which is selected from primary and/or secondary alcohols, carboxylic acids, carboxylic anhydrides, carboxylic esters, aldehydes, ketones (including hydroxyketones), nitriles, nitro compounds, organic nitrates and mixtures thereof or else from nitroalkanes, in particular nitromethane and/or nitroethane, each of which has at least 3 carbon atoms, in the presence of at least one catalyst, wherein the catalyst comprises an activated carbon substrate which is provided, in particular is doped, with at least one metal.

In addition, in the context of the present invention, it is preferred that the CH-acidic compound (B) has at least one acidic hydrogen atom on a carbon atom in the vicinal and/or alpha position to at least one carbon atom having at least one electron-withdrawing group and/or has at least one acidic hydrogen atom on a carbon atom in the geminal position to an electron-withdrawing group.

The expression "vicinal" or "geminal" defines in this case the position of the carbon atom carrying at least one acidic hydrogen atom and therefore the position of the acidic hydrogen atom to the electron-withdrawing group.

The expression "vicinal position" describes here in the context of the present invention, in particular that the carbon atom carrying the electron-withdrawing group is directly adjacent to the carbon atom carrying the acidic hydrogen, or is directly bound thereto.

The expression "geminal position", in contrast, in the context of the present invention is taken to mean that the electron-withdrawing group is bound to the carbon atom which also carries the acidic hydrogen.

The expression "alpha position", in the context of the present invention, is taken to mean a second carbon atom directly adjacent to a first carbon atom or directly bound thereto. If, for example, the carbon atom carrying an acidic hydrogen is situated in the alpha position to a carbon atom carrying an oxo group, then acidic hydrogen on the one hand and oxo group (i.e. electron-withdrawing group) on the other hand, are positioned or arranged vicinal to one another.

In the event that the acidic hydrogen atom is situated on a carbon atom in the vicinal and/or alpha position to at least one carbon atom having at least one electron-withdrawing group, it can be provided that the electron-withdrawing group is selected from oxo groups, hydroxyl groups, nitro groups and/or nitrate groups. Alternatively, in the event that the acidic hydrogen atom is situated in the geminal position to an electron-withdrawing group, it can be provided that the electron-withdrawing group is selected from nitrile groups, isonitrile groups, carbonyl groups, carboxyl groups, carboxylic ester groups and/or alcohol groups.

Expressed in other words, in the context of the present invention, it can therefore be provided that the CH-acidic compound has at least one carbon atom having at least one electron-withdrawing group and/or at least one electron-withdrawing group on the one hand, and also at least one acidic hydrogen atom on the other, wherein the acidic hydrogen atom can be situated on a carbon atom in the vicinal and/or alpha position to the carbon atom having at least one electron-withdrawing group or else can be situated in the geminal position to the electron-withdrawing group. In the event that the acidic hydrogen atom is situated on a carbon atom in the vicinal and/or alpha position to at least one carbon atom having at least one electron-withdrawing group, it can be provided in this case that the electron-withdrawing group is selected from oxo groups, hydroxyl groups, nitro groups and/or nitrate groups. In the event, in contrast, that the acidic hydrogen atom is situated in the geminal position to an electron-withdrawing group, the electron-withdrawing group can be selected from nitrile groups, isonitrile groups, carbonyl groups, carboxyl groups, carboxylic ester groups and/or alcohol groups.

Particularly good results are obtained in the context of the present invention if the CH-acidic compound (B) is selected from primary and/or secondary alcohols of the general formula (I)

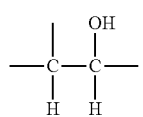

and/or
nitro compounds and/or organic nitrates of the general formula (II)

where X=$NO_2$, $ONO_2$
and/or
carbonyl compounds of the general formula (III)

and/or
nitrile compounds of the general formula (IV)

Particularly good results are obtained here when the primary and/or secondary alcohols correspond to the general formula (I')

where R=H, organyl, in particular alkyl, preferably $C_1$-$C_4$ alkyl,
and/or
when the carbonyl compounds correspond to the general formula (III')

where R=H; organyl, in particular $C_1$-$C_{15}$ alkyl, preferably $C_1$-$C_{10}$ alkyl, more preferably $C_1$-$C_6$ alkyl, particularly preferably $C_1$-$C_4$ alkyl; OH; $OR^1$ where $R^1$=alkyl, in particular $C_1$-$C_{15}$ alkyl, preferably $C_1$-$C_{10}$ alkyl, more preferably $C_1$-$C_6$ alkyl, particularly preferably $C_1$ and/or $C_2$ alkyl, aryl, arylalkyl, alkylaryl.

In this connection, in said classes of compounds, cyclic compounds can also be used, in particular those in which the electron-withdrawing group is directly bound to the ring system or is part of the ring system.

Although the present invention principally relates to the condensation of organic compounds having more than three carbon atoms, it can be provided according to the invention that additionally added to the reactants are lower alcohols, in particular methanol and/or ethanol, preferably ethanol, which then participate in the reaction. The lower alcohols, in particular ethanol, can either be added to the reactants, or else already be present therein from the start. For instance, in the context of the present invention, for example fermentation products of glucose or cellulose such as, acetone, butanol and ethanol, for example, what are termed ABE products, can be added or used as reactants. The presence of lower alcohols also increases the conversion rate of the condensation or coupling reaction and simultaneously improves the total product selectivity.

Furthermore, it has proved advantageous in the context of the present invention, if water is added to the reactants. As a result of the presence of water during the reaction, in particular the product selectivity may be controlled in a targeted manner, in particular markedly increased.

For the method according to the invention, or the process procedure according to the invention, the presence of water is firstly non-critical, that is to say the method is not adversely affected; secondly, the product selectivity can even be further improved. This has the result, for example, that fermentation products or industrial waste products can be used as reactants in the method according to the invention without particular purification steps, in particular without the complete or predominant removal of water fractions, wherein the use of such water-containing reactant mixtures is, according to the invention, even to be preferred compared with pure and water-free reactants. As a result, time and energy can be saved, whereby the economic and ecological resources are less burdened.

Using the method according to the invention, methanol and ethanol or higher alcohols from synthesis gas production, such as from the Fischer-Tropsch alcohol process, and all alcohols or mixtures thereof produced by fermentation can also be utilized as feedstocks. Precisely this makes the method according to the invention markedly more flexible than methods of the prior art. In particular, it is advantageous that alcohols produced by fermentation, alone or in combination with other bio-based alcohols, can also be utilized, and even can be used directly in the method according to the invention as an azeotrope with water, and so complex removal of water before the method according to the invention is carried out is unnecessary.

Particularly advantageously, and sustainably, the method according to the invention may be carried out when what are termed fusel alcohols from the fermentation of waste streams or from the fermentation of carbon monoxide, such as from converter gas from steel production, are used as raw material. In addition, it is advantageous that the water in the fusel alcohols obtained from the fermentation even promotes the selectivity of the alcohol condensation to form alkanes.

On account of the good water tolerance of the method according to the invention, it is also possible to use directly the mixtures formed in a fermentation such as, for example, acetone/butanol/ethanol (ABE synthesis), in particular after an upstream reduction of the water content.

It is likewise advantageous that using the method according to the invention, $C_4$-$C_8$ alcohols can be converted which were previously produced from the condensation of ethanol alone or in a mixture with methanol, and can additionally also contain aldehydes and water.

According to a particular embodiment of the present invention, it can be provided that the organic compound (A) containing at least one oxo and/or hydroxyl function firstly, and the CH-acidic compound (B) secondly, are identical. In the context of the present invention, it is therefore possible also to carry out what are termed autocondensation reactions, in particular of alcohols, aldehydes or ketones.

In addition, by adding secondary n-alcohols or oxidation products thereof such as 2-propanol or acetone, two molecules of an alcohol can be coupled to the particular carbon atoms adjacent to the functional group of the secondary alcohol or of the ketone, which markedly increases the flexibility with respect to the possible reaction products. The use of branched alcohols and oxidation products thereof is also possible in this case.

In particular it is also possible in the context of the present invention to condense secondary alcohols and/or ketones, such as, for example, 2-propanol or acetone, with branched longer-chain primary and/or secondary alcohols, in particular Guerbet alcohols, such as 2-ethylbutanol, 2-ethyloctanol, etc., for example. In this manner, more highly branched products of the method, in particular alcohols and alkanes, can be obtained, the melting points of which, compared with the unbranched products, are usually decreased by 10° C. or more. Such products are suitable particularly for use as aviation gasoline, in particular kerosene, or precursor substances or precursors thereof.

The coupling or condensation reactions proceeding in the process procedure according to the invention may be illustrated hereinafter by way of example with reference to the reaction equations (1) and (2) hereinafter.

Reaction equation (1) describes the reaction according to the invention of n-hexanol with acetone firstly ("synthesis a)") and also with 2-propanol secondly ("synthesis b)"). In both variants of the process procedure, identical compounds are obtained, wherein the ketone or the secondary alcohol act as CH-acidic compound. From the coupling reaction of n-hexanol with acetone or 2-propanol, the two-fold condensation product is obtained as main product, whereas the single condensation product and also an oxidation product of n-hexanol, namely hexanal, are obtained as principle by-products.

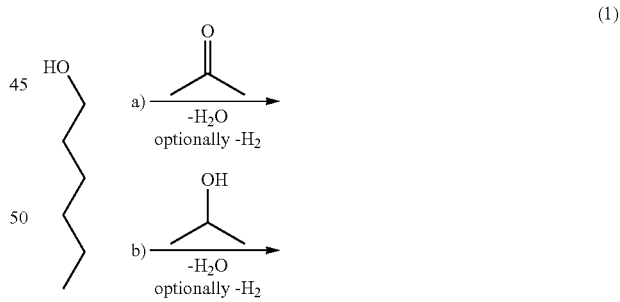

(1)

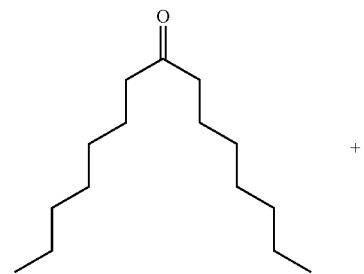

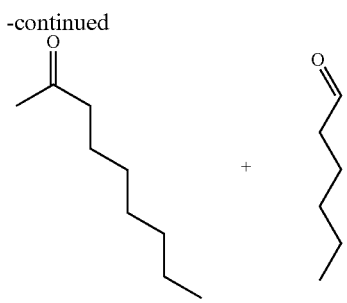

Reaction equation (2), in contrast, denotes the production of what are termed Guerbet alcohols and also of branched alkanes, for example of the autocondensation of n-hexanol.

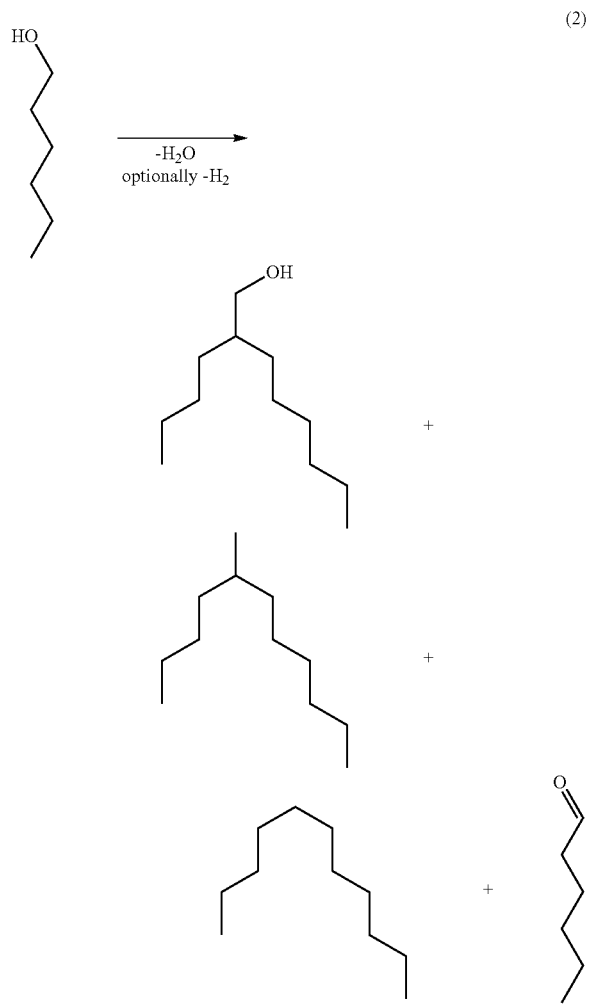

Not only reaction equation (1) but also reaction equation (2) only reflect the respective reaction course in a simplified manner, wherein not all of the products formed are listed in the reaction equations.

However, not only the choice of reactants, but also the further process parameters, have a great effect on the efficiency and selectivity of the method according to the invention, and also on the yield and product distribution:

Generally, the method, in the context of the process procedure according to the invention, is carried out in the gas phase and/or in the liquid phase and/or in the supercritical range, wherein a process procedure in the gas phase is preferred.

In addition, it can be provided that the method is carried out above the boiling temperature of the reactants and/or of the products, preferably above the boiling temperatures of the reactants and products.

Particularly good conversion rates, yields and selectivities are obtained when the method is carried out at temperatures in the range from 150° C. to 600° C., in particular 250 to 450° C., preferably 300 to 400° C.

In addition, in the context of the present invention, the method can in principle be carried out at reduced pressure, at atmospheric pressure, or at elevated pressure. In this connection, however, it has proved to be particularly advantageous when the method is carried out at atmospheric pressure or at elevated pressure; if the method is carried out at atmospheric pressure or at elevated pressure, the absolute pressure is generally in the range from atmospheric pressure to 150 bar, in particular in the range from atmospheric pressure to 80 bar, preferably in the range from atmospheric pressure to 25 bar.

As already discussed above, an increase in pressure and/or of the temperature generally effects an increase in the conversion rates, wherein, however, the increase in the conversion rate, from a certain point, is achieved at the cost of selectivity, and so, in each case, the optimal matching of the individual process parameters with one another must be determined.

Also, the reaction times or the contact times have a great effect on the conversion rates and yields on the one hand, and the selectivity of the product formation on the other. Generally, the method is carried out with reaction times and/or contact times in the range from 0.01 min to 12 hours, in particular 0.1 min to 10 hours, preferably 1 min to 5 hours.

If the method is carried out in the gas phase and/or in the supercritical range, it has proved suitable if the method is carried out with reaction times and/or contact times in the range from 0.001 to 120 seconds, in particular 0.001 to 60 seconds, preferably 0.05 to 30 seconds.

If, in contrast, the method according to the invention is carried out in the liquid phase, good results are obtained when the method is carried out with reaction times and/or contact times in the range from 0.001 min to 12 hours, in particular 0.1 min to 10 hours, preferably 1 min to 5 hours.

In the context of the present invention, it can—as discussed above—be additionally provided that the method is carried out in the presence of water, preferably in the form of steam, and/or in the presence of hydrogen. The water in this case can be formed on the one hand during the condensation or coupling reaction, and/or on the other hand can be added to the reactants or in the course of the process procedure, wherein the presence of a certain amount of water markedly increases the product selectivity of the condensation reaction or of the coupling reaction.

Equally, it is also possible to carry out the reaction in the presence of hydrogen, wherein generally, hydrogen is equally formed in the course of the reaction. However, if hydrogen is additionally added, via hydrogenation reactions, the fraction of aldehydes and ketones in the resultant product mixture can be reduced or minimized, wherein at the same time, the fraction of alcohols and alkanes is increased or maximized.

In the context of the method according to the invention, inert gases, in particular nitrogen and/or argon, preferably nitrogen, can also be additionally added to the reactants or starting materials, if this is desirable or required. The addition of the inert gases proceeds, in particular, for dilution purposes, which is frequently accompanied with an improved product selectivity.

Alternatively, or in supplementation, the method according to the invention can also be carried out in the presence of further gases. For instance, to the reactants, or during the process procedure, for example short-chain alkanes, in particular linear $C_1$-$C_6$ alkanes, can be added, which effect an improvement in the heat transfer and the selectivity.

It is equally possible to add carbon monoxide and/or carbon dioxide to the reactants, or while the method is being carried out; these substances can act as further possible reaction partners during the reaction.

The presence of gases makes possible, in particular, a less complex and more efficient separation of the product mixture, if this is desired.

Generally, it is preferred, however, in the context of the present invention if merely only slightly dilute, but preferably undiluted, reactants or reactant mixtures are used, and also during the process procedure, no gases, except for hydrogen, are added, since in this manner the highest space-time yields and the greatest space velocities can be achieved.

The method of the invention can be operated in principle discontinuously, i.e. batchwise, or else continuously. Preference, in particular in the case of technical or industrial application, is given to a continuous process procedure, which makes possible high space-time yields or space velocities and conversion rates, and therefore can be carried out particularly economically.

Generally, the method according to the invention is carried out with a space-time yield, reported as amount of all products formed per volume of catalyst and per unit time, in the range from 10 to 3000 g/(liter·h), in particular 25 to 2500 g/(liter·h), preferably 30 to 2000 g/(liter·h), particularly preferably 50 to 1500 g/(liter·h).

Another measure of the high efficiency and capability of the method according to the invention are the space velocities that can be achieved. The method according to the invention is generally carried out at a space velocity, reported as amount of substance of all products formed per mass of catalyst and per unit time, in the range from 0.1 to 100 mol/(kg·h), in particular 0.5 to 25 mol/(kg·h), preferably 1.0 to 20 mol/(kg·h), particularly preferably 1.25 to 18 mol/(kg·h), very particularly preferably 1.5 to 15 mol/(kg·h).

In addition, it can be provided that the method is carried out with a conversion rate based on amount of substance, based on the reactants used, in the range from 15 to 100%, in particular 20 to 90%, preferably 30 to 80%, particularly preferably 40 to 75%.

The above-cited space-time yields and space velocities and also the conversion rates based on amount of substance describe ranges in which the method according to the invention can be carried out particularly economically and favorably according to process economics aspects, wherein high selectivity is achieved in the resultant product mixtures.

As already discussed above, in the context of the method according to the invention, a catalyst based on a metal-loaded activated carbon substrate is used.

The activated carbon used in the context of the present invention preferably contains not only carbon, but also small amounts of oxygen, nitrogen, sulfur and hydrogen, which are chemically bound in the form of various functional groups, such as carbonyl, carboxyl, phenol and ether groups, and also lactones and quinones. These surface oxides can result from the raw materials, but they can be formed by the activation process, by the effect of chemical activators, and also by the effect of oxygen or steam. The chemical properties of the surface play a significant role for the adsorption and catalysis.

The starting materials for activated carbon which are suitable for producing catalysts that are usable according to the invention, generally possess mineral components which can be concentrated during the activation process. In addition, it is also possible that inorganic chemicals are not completely removed for the activation of the activated carbon or remain entirely on the activated carbon.

The ash content of activated carbons is definitively determined by the mineral components. The main components of these ashes are alkali metals and alkaline earth metals, usually in the form of carbonates and phosphates, optionally together with silica, and also oxides of iron and aluminum. The ash content of activated carbons can be reduced by washing with water or acid. Commercial products therefore have ash contents of less than one to twenty percent.

Activated carbon acts simultaneously as catalyst and as catalyst support: the catalytic activity of the activated carbon as such is substantially based on the structure of the carbon skeleton which consists of a mixture of amorphous and graphite-like carbon; at the rim of layers there are many chemically unsaturated corners and edges which act as what are termed lattice vacancies, and on the internal activated carbon surface of the activated carbon used in the context of the method according to the invention, there lie preferably the abovementioned surface oxides which can participate in redox reactions and are sometimes the reason for the chemical activity of activated carbons. In addition, the activated carbons used according to the invention act as supports for the metal doping.

The catalyst used for carrying out the method according to the invention and/or the activated carbon substrate used are generally finished and/or formed so as to be basic.

In particular, it can be provided that the catalyst and/or the activated carbon substrate has at least one basic functional group and/or at least one basic chemical compound.

In this case, it has proved, in particular, as particularly advantageous when the basic finishing is provided by (i) hydroxides; (ii) oxides; (iii) salts of inorganic acids, in particular phosphates, sulfates, carbonates, and nitrates; (iv) salts of organic acids, in particular lactates, phthalates, formates and acetates; and/or (v) alcoholates.

According to a preferred embodiment of the present invention, the basic finishing is provided by carbonates and/or phosphates, particularly preferably by carbonates and phosphates.

The basic finishing in this case can be performed during production of the catalyst or else retrospectively, in particular by means of impregnation. Particularly good results, however, are obtained in the context of the present invention when the basic finishing is performed during production of the catalyst.

A basic finishing, in the context of the present invention, is taken to mean that the catalyst or the activated carbon substrate has basic groups and/or compounds or else basically reacting groups and compounds. It is decisive that the basic character of these groups or compounds is retained under reaction conditions in the finished catalyst. In this case it is absolutely possible that the compounds originally used are converted during the catalyst production or else in the catalytic reaction; in this case, the conversion products must have a basic character. Thus, for example, carbonates, during an activation of the activated carbon substrate, can react to form oxides, but, it is also equally possible that the carbonates react with the carbon backbone of the activated carbon substrate, for example forming phenolates, oxides, anhydrides, hydroxides etc.

Furthermore, the catalyst used according to the invention should have a high specific surface area. The catalyst used in the context of the method according to the invention and/or the activated carbon substrate generally has a specific surface area (BET) in the range from 450 to 3000 m²/g, in particular 500 to 2500 m²/g, preferably 600 to 2250 m²/g, particularly preferably 900 to 1700 m²/g, very particularly preferably 950 to 1500 m²/g, still more preferably 1000 to 1350 m²/g.

Furthermore, the catalyst used according to the invention should have a large micropore volume. In particular, it can be provided that the catalyst and/or the activated carbon substrate has a micropore volume, in particular a micropore volume according to Gurvich, in the range from 0.1 to 3.0 ml/g, in particular 0.2 to 2.5 ml/g, preferably 0.25 to 1 ml/g, particularly preferably 0.3 to 0.7 ml/g.

In addition, in the context of the present invention it has proved to be advantageous when the catalyst and/or the activated carbon substrate has a service life of at least 10 days, in particular at least 20 days, preferably at least 30 days, particularly preferably at least 6 months. Long service lives of the catalyst used according to the invention permit the method according to the invention to be carried out continuously on a large scale and therefore permit production of higher alcohols and aldehydes which is favorable from an economic aspect.

Equally, it has proved advantageous when the catalyst and/or the activated carbon substrate comprises at least one functional group, preferably a polar and/or ionic functional group. In this case, it can be provided that the at least one functional group is selected from carbonyl, carboxylate, hydroxyl, oxide, ether, ester, lactone, phenol and/or quinone groups. The abovementioned functional groups can be formed, for example, by reactions of the carbon backbone of the activated carbon substrate with a compound required for the basic finishing during the activation of the activated carbon substrate (as described above).

Generally, the metal, in particular the metal doping, of the catalyst used in the context of the method according to the invention, is selected from the group of alkali metals, alkaline earth metals, metals of the subgroups of the Periodic Table of the Elements and the rare earths, and also mixtures or combinations thereof.

In addition, it can be provided that the catalyst comprises at least one monovalent metal $M^I$, in particular at least one alkali metal, preferably sodium and/or potassium, and/or at least one divalent metal $M^{II}$, in particular calcium and/or magnesium, particularly preferably at least one monovalent metal $M^I$ and at least one divalent metal $M^{II}$.

Equally, it can be provided that the catalyst contains phosphorus, in particular in the form of phosphates.

Particularly good results are obtained in the context of the method according to the invention when the abovementioned compounds and/or substances are present in specific molar ratios to one another in the catalyst used according to the invention. In this connection, it is preferred in the context of the present invention when the following molar ratios apply:
(i) $0.5 \leq M^I/M^{II} \leq 5$, in particular $2 \leq M^I/M^{II} \leq 3$; and/or
(ii) $2 \leq M^{II}/P \leq 30$, in particular $2 \leq M^{II}/P \leq 8$; and/or
(iii) $1 \leq M^I/P \leq 60$, in particular $5 \leq M^I/P \leq 10$; and/or
(iv) $1 \leq K/Na \leq 20$, in particular $10 \leq K/Na \leq 20$; and/or
(v) $1 \leq Ca/Mg \leq 10$, in particular $4 \leq Ca/Mg \leq 6$.

Equally, in the context of the method according to the invention, very good results are obtained when the catalyst comprises the following quantitative fractions (percentages by weight) of the components cited hereinafter, wherein the details hereinafter are in each case based on the catalyst:
(i) $M^I$, in particular sodium and/or potassium, preferably sodium and potassium: 0.1 to 20% by weight, in particular 0.2 to 15% by weight, preferably 0.5 to 10% by weight; and/or (ii) $M^{II}$, in particular calcium and/or magnesium, preferably calcium and magnesium: 0.1 to 20% by weight, in particular 0.2 to 10% by weight, preferably 0.5 to 5% by weight; and/or
(iii) P, in particular in the form of phosphate, calculated as phosphorus P: 0.01 to 5% by weight, in particular 0.02 to 2.5% by weight, preferably 0.02 to 1% by weight.

Particularly good conversion rates, yields and selectivities can be achieved in the context of the method according to the invention when the catalyst used according to the invention contains the abovementioned metals and phosphorus not only in the specific molar ratios to one another but also in the respective absolute amount of substance fractions.

In particular, in the context of the present invention, it can be provided that, as catalyst, an activated carbon that is finished and/or established so as to be basic, and which is provided with at least one alkali metal and/or alkaline earth metal doping, preferably alkali metal and alkaline earth metal doping, particularly preferably potassium and calcium and/or magnesium doping, is used. In this case, it has proved to be particularly advantageous when an activated carbon which is established with phosphate and/or carbonate so as to be basic, and is doped with potassium and calcium and/or magnesium is used.

According to a particular embodiment of the present invention, as catalyst, a shaped activated carbon can be used, such as that in DE 10 2004 033 561 A1 and DE 10 2004 033 561 B4, the entire respective disclosure thereof is hereby incorporated in entirety by reference.

According to this embodiment, as catalyst, a shaped activated carbon is used which can be produced by a method for producing shaped activated carbon from a carbon substrate, a binder, and a catalytic component of the general formula (I)

$$[M]_{m3}[AO_{n4}]_{m4} \quad (I)$$

wherein
M denotes a cation and is selected from the group of alkali metal cations or alkaline earth metal cations;
m3 and m4 denote stoichiometric coefficients having integers where m3≥1 and m4≥1;
[$AO_{n4}$] denotes an oxygen-containing anion having integral stoichiometric coefficients n4≥1;
[$AO_{n4}$] is preferably selected from the group of carbonates or hydroxides,
wherein the binder is obtained from the reaction of a water-soluble carbohydrate-containing starting material having a glucose content of≥50% by weight, in particular≥60% by weight, wherein the carbon substrate is first mixed with the catalytic component, wherein subsequently the mixture of catalytic component and carbon substrate is mixed with the binder, wherein the resultant mixture of carbon substrate, catalytic component and binder is compacted to give shaped bodies, and wherein the shaped bodies are carbonized and activated, wherein the binder is obtained from the reaction of the carbohydrate-containing starting material with an additive, wherein, for obtaining the binder, the additive is added to the carbohydrate-containing starting material before mixing the binder with the mixture of the carbon substrate and catalytic component; in this case the additive can be selected, in particular, from the group of phosphoric acids and/or salts thereof, sulfuric acids and/or salts thereof, and/or sulfuric acid derivatives and/or salts thereof.

This general production method and the chemical composition of the compounds of the metals, transition metals and rare earths in the doping are originally targeted at the adsorption of acid gases. To produce a particularly effective catalyst usable in the method according to the invention, this production method can be further slightly adapted, wherein the adaptations are disclosed in their entirety in DE 10 2004 033 561 A1 and/or DE 10 2004 033 561 B4.

As doping reagent for alcohol synthesis, for the shaped activated carbons for alcohol or aldehyde synthesis, metal salts are used, the cations of which are selected from metals of main group 1 and 2, the transition metals, the rare earths and the semimetals.

Preferably, $K_2CO_3$ is added to the carbon substrate as activator. Potassium carbonate reacts with the carbon substrate, inter alia, with carbon consumption, and leads to the formation of very small micropores which, during the gas activation with steam, are further expanded to form larger micropores and mesopores, and thus lead to the desired pore system. By varying the amount of $K_2CO_3$ in the carbon substrate and the activation conditions (temperature, steam amount, residence time etc), differing pore sizes and pore distributions may be set for that reason in the shaped activated carbon.

The additives provided, such as $K_2CO_3$, for instance, must be added to the carbohydrate-containing starting material of the binder, still before mixing the binder with the carbon substrate. The binder for producing shaped activated carbon is obtainable from the reaction of a water-based glucose-containing starting material with an additive, wherein the additive is selected from the group of phosphoric acids and/or salts thereof. The water-based glucose-containing starting material is preferably glucose or glucose derivatives, such as, preferably, glucose syrup, thick juice or fruit syrup. These sugar-containing starting materials are distinguished by a small ash fraction of<5% by weight, in particular<2% by weight, which likewise is advantageous for the properties of the shaped activated carbon. In principle, all carbohydrates, for example monosaccharides (in particular glucose, fructose, mannose, galactose etc) and/or disaccharides (in particular sucrose, maltose, lactose, cellobiose, trehalose etc) and/or tri-, tetra-, oligo- and polysaccharides (in particular starch, cellulose, glycogen etc) and/or predissolved starch or cellulose, in particular in the form of aqueous solutions, can be used as starting materials. Mixtures of the most varied sugars can also be used.

If the additive selected for reacting the water-based glucose-containing starting material to form a binder is phosphoric acid, it is preferably provided, and advantageous, that after mixing the phosphoric acid with the water-based glucose-containing starting material, the binder thus obtainable is not neutralized. If this binder is then, for producing shaped activated carbon, mixed with a carbon substrate, neutralization of acid groups of the binder with basic groups of the carbon substrate occurs. By dispensing with the process step of neutralization, the production complexity in producing the binder is markedly simplified. Furthermore, it is also possible, and likewise advantageous, to use a salt of phosphoric acid directly as additive to the water-based glucose-containing starting material in the production of the binder.

In the context of this embodiment, it is preferred when the additive corresponds to the general formula (II)

$$[M_{m1}][H_{n1}P_{n2}O_{n3}]_{m1} \quad (II)$$

wherein M denotes a proton (H$^+$) or a cation which is selected from the group of alkali metal, alkaline earth metal, ammonium, calcium, magnesium and iron ions, preferably from alkali metal, alkaline earth metal and ammonium ions, wherein H denotes hydrogen and P or O denotes phosphorus or oxygen, respectively,
wherein m1 and m2 denote stoichiometric coefficients and are integers where m1≥1 and m2≥1;

wherein [H$_{n1}$P$_{n2}$O$_{n3}$] denotes an anion having integral stoichiometric coefficients n1, n2 and n3 where n1>0, n2>1; n3>2.

As additive for the carbohydrate-containing or sugar-containing binder, in particular phosphoric acid (H$_3$PO$_4$) is suitable.

In the presence of phosphoric acids, the carbohydrate-containing starting material is dehydrated with the formation of carbon. This process is illustrated for the example of glucose in the following equation:

$$C_{12}H_{22}O_{11} \rightarrow 12C + 11H_2O$$

In this case a carbon modification is formed which—in comparison with the added carbon substrate (e.g. wood charcoal, carbonized fruit stones etc)—is attacked only slowly by steam.

Generally, carbonates, nitrates, sulfates or other organic salts can be used as precursors for forming the surface oxides, which form oxides with the action of high temperatures above 400° C., but preferably at activation temperatures of 500 to 950° C.

The additive can additionally be selected from (tri-)ammonium phosphate, (di-)ammonium hydrogenphosphate, ammonium dihydrogenphosphate, (tri-)potassium phosphate, (di-)potassium hydrogenphosphate, potassium dihydrogenphosphate, and also mixtures thereof:
(di-)ammonium hydrogenphosphate is particularly suitable as additive because of the high water solubility in a water-based glucose-containing starting material. In the reaction of the additive with the water-based carbohydrate-containing or glucose-containing starting material, for example (di-)ammonium hydrogenphosphate reacts catalytically with the sugar of the binder, wherein the sugar is aromatized in a plurality of reaction steps. The catalytic effect is based, in particular, in that phosphates can add or condense to the OH group of the sugar, with elimination of water, and then, with formation of a double bond in the sugar ring—finally with aromatization or olefinization—are eliminated.

If the activated carbon is activated by steam, the aromatized binder reacts substantially poorer with steam than the carbon substrate during activation of the shaped activated carbon. The aromatization process of the sugar proceeds substantially catalytically, wherein the ash fraction in the activated carbon does not increase or increases only insignificantly.

The carbon substrate is preferably carbon from renewable raw materials, in particular wood charcoal or other lignocellulose-based natural materials. However, in principle, it is also possible to mix fossil carbon substrates, in particular brown coal and/or brown coal coke, and/or hard coal and/or mixtures of renewable and fossil carbon substrates, with the binder to produce shaped activated carbon. In addition, synthetic polymers, for example based on polyvinylbenzene or the like, synthetic polymers containing heteroatoms can also be used as carbon substrates.

The shaped activated carbon used according to this embodiment contains the catalytically active components or doping materials homogeneously distributed in a carbon-containing matrix. On account of the high temperatures prevailing during the production process, it may be assumed that the doping materials are in part and/or completely chemically modified. For example, the dissociation pressure of potassium carbonate is about torr in accordance with the subsequent equilibrium at 1000° C.:

$$K_2CO_3 \leftrightarrow K_2O + CO_2$$

In addition, it is known that potassium carbonate, together with the carbon substrate, forms surface complexes which contain C—O—K fragments. Likewise, in the specialist literature, the formation of intercalation compounds is postulated, in which, in particular metallic potassium is positioned at intermediate lattice sites of a graphite lattice structure. X-Ray structural analyses of activated carbons show that carbon may be encountered not only in the amorphous form, but also in the form of very small crystals which have the usual graphite lattice structure.

Therefore, it may be assumed—without wishing to be bound by this theory—that the shaped activated carbons in the active centers formed from the doping materials no longer have the doping materials originally used, but at least in part units, in particular clusters and intercalation compounds, having a different chemical structure. It may be assumed that the intercalation compounds are only restricted to the graphite lattice structure.

It is further known that intercalation compounds form with the alkali metals and alkaline earth metals, which act as very strong reducing agents and at the same time also actively participate in hydrogen storage and hydrogen transfer reactions.

For further details in this regard on the catalyst according to this embodiment, reference is made to DE 10 2004 033 561 A1 and also DE 10 2004 033 561 B4.

According to a further alternative particular embodiment of the present invention, as catalyst, a shaped activated carbon can be used, as is described in DE 10 2006 025 450 A1, or in WO 2007/137856 A2 which belongs to the same patent family, the entire respective disclosure of which is hereby incorporated in entirety by reference.

According to this embodiment, therefore, as catalyst, a shaped activated carbon is used, which can be produced from a compactable mass which contains a ground carbon-containing material, a binder and at least one metal-containing doping reagent, and which is compacted, dried, carbonized, and subsequently activated by means of an activation gas, wherein a first doping reagent is present, wherein the first doping reagent is a metal salt, the metal of which is selected from the group of metals of main groups 3 to 6 of the Periodic Table of the Elements, transition metals, rare earths and semimetals and/or wherein the first doping reagent is an iodide of the alkali metals or alkaline earth metals, and wherein optionally a second doping reagent of the formula $M^2_p(EO_q)_r$ is present, wherein $M^2$ is selected from alkali metals and alkaline earth metals, E is an element of main groups 3 to 7 of the Periodic Table of the Elements and p, q and r in each case are integers ≥1; in this case the second doping reagent can in particular be selected from hydroxides and carbonates.

In the course of the reaction procedure, it is observed, in particular, that the catalyst, presumably due to addition of alcoholates, increases in weight. This increase in weight is in particular approximately 10 to 15% by weight. In particular, on the catalyst surface—without wishing to be bound by this theory—equilibria between various adsorbed compounds, in particular alcoholates, appear to form.

As already described above, the method according to the invention serves in particular for producing higher alcohols, aldehydes, ketones and alkanes, and also for producing aromatics. Generally, when the method according to the invention is carried out, as product or product mixture, alcohols, in particular branched, preferably branched primary alcohols, and/or aldehydes and/or ketones and/or alkanes and/or aromatics and also mixtures thereof are obtained. As far as the chain length or number of carbon atoms of the products are concerned in this context, in the process procedure according to the invention, usually, as product or product mixture, $C_5$-$C_{35}$ compounds, in particular $C_5$-$C_{30}$ compounds, preferably $C_6$-$C_{25}$ compounds, more preferably $C_6$-$C_{20}$ compounds, are obtained.

In addition, in the context of the present invention it can be provided that, during the reaction or in the process procedure, water and optionally hydrogen, in particular water and hydrogen, are generated. In this connection, it has proved particularly favorable if, per mole of compound (A) used, at least one mole of water is generated. As already described above, the presence of water during the reaction procedure has the advantage that the selectivity of the product can be adjusted or improved in a targeted manner. In this case it is irrelevant whether the water originates from the reaction, is present in the reactants or reactant mixtures, or is additionally introduced.

According to a particular embodiment of the present invention, the resultant product or product mixture can then be subjected to a hydrogenation process step and/or a hydrotreating process step, preferably a hydrotreating process step.

In the context of conventional hydrogenation methods, such as, for example, using Raney nickel, the aldehydes and ketones resulting in the process procedure can be reduced to alcohols, whereas using a hydrotreating process, all compounds, that is to say also oxygen-containing and/or nitrogen-containing and/or sulfur-containing compounds, are reduced to alkanes. Hydrotreating is a method routinely carried out in the course of crude oil refining, which is known to those skilled in the art and therefore requires no further explanation.

A further peculiarity of the method according to the invention is considered to be that, via the specific selection of reactants or reactant mixtures, such as, for example, mixtures of various alcohols and ketones of, in each case, known chain length or known composition of the mixtures, particular statistical product distribution can be obtained and, in particular, adjusted in a targeted manner. In this manner, it is possible to obtain special product mixtures having a specific statistical product distribution specified in advance.

The hydrogenated products or product mixtures are, in particular, compounds which can preferably be used as combustibles or transport fuels. Thus, for instance, in a condensation carried out solely with butanol, by subsequent hydrogenation of all aldehydes which are formed in this reaction as by-products, under moderate conditions (200° C., 30 bar, Raney-nickel catalyst) and preferably using the hydrogen formed in the system and after separating off water by phase separation, an alcohol/alkane fraction can be obtained which can be used as gasoline suitable for motors.

When longer-chain alcohols are used, for instance butanols, pentanols, hexanols or higher alcohols or mixtures thereof, as sole reactants, in each case with or without ethanol fractions, the resultant reaction mixture, optionally after prior separation of low-boiling fractions, can be converted directly by what is termed hydrotreating in one step into a kerosene fraction containing only alkanes. The products thus obtainable cannot be differentiated in principle in their physical properties from aviation kerosene that is fossil-generated and conforms to JET-A1.

Owing to the high fraction of alkanes possible in a product mixture obtainable by the method according to the invention, a considerable amount not only of hydrogen, but also of reactor volume can be saved in a subsequent hydrotreating of the mixture to give a product consisting only of alkanes, such as Jetfuel for instance. As a result of the targeted selection of chain length, e.g. of the alcohols, and the type thereof, i.e. primary, secondary, branched or n-alcohol, and also any desired mixtures thereof, the desired boiling point and chain length distribution of the kerosene fraction can be set or influenced in a targeted manner. In addition, in this manner, cost advantages result owing to savings in time and energy, since no mixture having a broad distribution of boiling points needs to be distilled in a complex manner, as is customary, for example, in the case of products having broad statistical carbon chain distributions produced via Fischer-Tropsch syntheses.

In addition, the mixture of alcohols and alkanes can be subjected to a catalytic dehydration, followed by a hydrogenation, in order to obtain a mixture containing only alkanes, which is suitable for Jetfuel.

The present invention further relates—according to a second aspect of the present invention—to a product or product mixture, in particular alcohols, aldehydes, ketones, alkanes and/or aromatics, and also mixtures thereof, which are obtainable by the method described above.

Particularly good results are obtained in this case in the context of the present invention when the product or product mixture comprises $C_5$-$C_{30}$ compounds, in particular $C_5$-$C_{30}$ compounds, preferably $C_6$-$C_{25}$ compounds, more preferably $C_6$-$C_{20}$ compounds.

If, in the context of the method according to the invention, a hydrogenation process step, or a hydrotreating process step is carried out, preferably a hydrotreating process step, it can be provided that the product or product mixture comprises a mixture of preferably branched alkanes, in particular $C_5$-$C_{30}$ alkanes, preferably $C_5$-$C_{25}$ alkanes, more preferably $C_6$-$C_{25}$ alkanes, particularly preferably $C_6$-$C_{20}$ alkanes. Such a product or product mixture can be used, for example, as kerosene for aviation turbines.

If the reactants used, in particular alcohols, are selected in such a manner that the resultant products chiefly contain 8 to 16 carbon atoms, the alkanes and alkenes generated, and also the alkanes which can be generated by hydrotreating the alcohols, come in the boiling and freezing point ranges thereof, into the specifications of Jetfuel A1, i.e. the familiar standard for aviation gasoline or kerosene used for civil purposes. Therefore, the invention also offers the possibility to produce in a targeted manner semifossil-identical kerosene completely from renewable raw materials, since the alcohols used in turn can be produced via catalytic condensation of bio-based ethanol or a combination of ethanol and methanol.

It is likewise advantageous that, in the method according to the invention, in addition to only few linear alkanes, also, in particular, longer branched alkanes form, or can be formed by hydrotreating Guerbet alcohols. According to the prior art, in contrast, branched alkanes must usually be generated in a complex manner from linear alkanes via a separate isomerization step, e.g. in a refinery, which is designed separately for the production of kerosene according to the standard Jetfuel A1.

In addition, depending on the reaction conditions, in particular from aldehydes, aromatic compounds having one or more alkyl groups are formed, which aromatic compounds are likewise advantageous for use in Jetfuel, since these compounds are present at up to 25 percent by mass in fossil kerosene, but do not occur in products which are obtained by Fischer-Tropsch synthesis or via hydrogenation of fats and oils.

If, in the context of the method according to the invention, product mixtures, in particular product mixtures of, in particular, higher alcohols (e.g. "Guerbet alcohols") and alkanes etc., are produced, the individual compounds or classes of compounds can be separated off or isolated by methods which are known per se to those skilled in the art, if desired or necessary. For example, oxygenated compounds or oxygen-containing compounds can be separated off from hydrocarbon fractions according to the method described in U.S. Pat. No. 7,465,846 B2. This is familiar per se to those skilled in the art, and so further details do not need to be given in this regard.

For further details on this aspect of the invention, reference can be made to the above descriptions on the first aspect according to the invention, which also apply correspondingly in relation to this aspect of the invention.

Again, the present invention further relates to—according to at third aspect of the present invention—the use of a product or product mixture according to the invention as defined above, as combustible and/or transport fuel in combustion machines, in particular in combustion engines preferably suitable for motor vehicles, preferably in gasoline engines and/or Wankel engines, and/or diesel engines, preferably as diesel or gasoline.

If the product or product mixture according to the invention, however, is subjected to a hydrotreating process step, this product or product mixture can be used as combustible and/or transport fuel, also in combustion machines, in particular in turbines suitable for aircraft, preferably in aviation turbines, preferably as kerosene.

Equally, it can be provided that the abovementioned products or product mixtures are used as solvent, as fragrance compounds and aroma compounds, as combustible and/or transport fuel for combustion machines, as wetting agent and in the cosmetics industry.

For further details on this aspect of the invention, reference can be made to the descriptions for the other aspects of the invention which apply correspondingly.

Finally, the present invention further relates—according to a fourth aspect of the present invention—to the use of an activated carbon substrate provided, in particular doped, with a metal, as catalyst for the catalytic condensation and/or coupling of organic compounds containing at least one oxo and/or hydroxyl function with CH-acidic compounds, in particular for generating higher alcohols, aldehydes, ketones, aromatics and/or alkanes, and also mixtures thereof.

For further details in this regard on this aspect of the invention, reference can be made to the above descriptions on the remaining aspects of the invention which apply correspondingly in relation to this use according to the invention.

Further designs, modifications and variations and also advantages of the present invention are readily recognizable and achievable to a person skilled in the art on reading the description, without departing in this case from the context of the present invention.

The present invention is illustrated with reference to the following exemplary embodiments which, in no case, however, restrict the present invention.

Exemplary Embodiments:
Catalyst Systems Used

In the preceding exemplary embodiments, as catalysts, alkali metal- and alkaline earth metal-doped activated carbon substrates made basic by means of phosphate are used, as are obtained according to DE 10 2004 033 561 A1. The catalyst systems used "Cat1", "Cat2" and "Cat3" are characterized chemically in more detail hereinafter:

Chemical composition of the catalyst systems used, based on ash:

| Cat1: | |
|---|---|
| ash content | 24.4% by weight |
| sodium | 7.28 g/kg |
| potassium | 238 g/kg |
| magnesium | 11.7 g/kg |

-continued

| Cat1: | |
|---|---|
| ash content | 24.4% by weight |
| phosphorus | 19.2 g/kg |
| calcium | 167 g/kg |
| total | 443.18 g/kg |

| Cat2: | |
|---|---|
| ash content | 18.1% by weight |
| sodium | 10.7 g/kg |
| potassium | 360 g/kg |
| magnesium | 13.9 g/kg |
| phosphorus | 36.5 g/kg |
| calcium | 110 g/kg |
| total | 531.1 g/kg |

| Cat3: | |
|---|---|
| ash content | 11.0% by weight |
| sodium | 22.2 g/kg |
| potassium | 307 g/kg |
| magnesium | 11.8 g/kg |
| phosphorus | 5.6 g/kg |
| calcium | 130 g/kg |
| total | 476.6 g/kg |

Molar chemical composition of the catalysts tested:

| | Na | K | Mg | Ca | P | | |
|---|---|---|---|---|---|---|---|
| Cat1 | Na | K | Mg | Ca | P | 0.5 Na/P | 0.8 Mg/P |
| | 0.3 | 6.1 | 0.5 | 4.2 | 0.6 | 9.8 K/P | 6.7 Ca/P |
| Cat2 | Na | K | Mg | Ca | P | 0.4 Na/P | 0.5 Mg/P |
| | 0.5 | 9.2 | 0.6 | 2.7 | 1.2 | 7.8 K/P | 2.3 Ca/P |
| Cat3 | Na | K | Mg | Ca | P | 5.3 Na/P | 2.7 Mg/P |
| | 1.0 | 7.9 | 0.5 | 3.2 | 0.2 | 43.5 K/P | 18.0 Ca/P |

Experimental Procedure

Pellets produced according to the invention of shaped activated carbon (cf. above description of the catalyst systems used) are mechanically comminuted and the fragments (1-2 mm fraction) are charged as catalysts into a stainless steel reactor. The reactor has an inner diameter of 21 mm and a volume of 75 ml. The mass charged is 30 g.

As starting materials or reactants, not only anhydrous but also aqueous, linear and branched alcohols come into consideration. Likewise, mixtures of various alcohols, various aldehydes and ketones are possible.

A schematic depiction of the experimental setup used is depicted in the single FIGURE: the reactants are situated in a pressure vessel 1 and are metered via a calibrated mass flow controller 2. Before entry into the evaporator, optionally an inert gas, generally nitrogen, can be added. The volumetric flow rate is adjusted via a needle valve using a rotameter and is typically between 0 and 40 Nl/h. In an electrically heated tube 3, the reactants are vaporized and heated to 345° C., or optionally also above. The inert gas is likewise heated to 345° C. or optionally also above. The gaseous mixture flows from the evaporator in the reactor 4 where the reaction proceeds on the surface of the catalyst. Typical contact times are between 0.01 and 30 seconds, when the reaction proceeds in the gas phase. Downstream of the reactor, the product mixture condenses 7 and the fraction which is not condensable at room temperature is removed in the gaseous state. Via a heated conduit, a direct sampling from the product gas stream is possible.

The composition of the liquid products is determined using an HPLC 1200 having an RI detector and a Rezex ROA, 300×7.8 mm column of Phenomenex from Agilent and the water content of the sample is determined by Karl-Fischer titration. For determination of further products, a GC/MS+ FID 6890N/5975 having a DB-FFAP, 30 m×0.25 mm×0.25 μm column from Agilent is used.

Selected experimental results are displayed in the following Tables 1 to 4. Apart from the compounds listed there, in addition principally water from the reaction is found in the product.

In addition to the liquid phase, the composition of the resultant gaseous product is also determined. The analyses show that, here, hydrogen and carbon dioxide form the main fractions (in mol %). Further components are alkanes and alkenes of various chain lengths. Overall, however, only a very small fraction of gaseous product (<5% by weight) is formed, especially at temperatures below 350° C. With increasing temperature or residence time, the fraction, however, can rapidly increase, depending on the materials used.

In order to carry out experiments at elevated pressure also, a system was used in which the reactant is transported by means of an HPLC pump from a reservoir into an evaporator heated with oil to 300° C. The reaction proceeds in a reactor heated electrically up to 345° C. or above (having a volume of 120 ml) in the presence of 50 g of the catalyst described. The product is condensed downstream of the reaction in two water-cooled heat exchangers. With this system, experiments were carried out at pressures up to 60 bar (absolute). A carrier gas is not used. The results of these experiments are likewise displayed in Table 1 and are characterized there as liquid-phase experiment (experiment No. 6).

TABLE 1

Self-condensation of n-hexanol

| Number | Reactant | Reactor temperature [° C.] | Pressure (relative) [bar] | Catalyst loading [mmol/ h · g (Cat)] | Throughput [g/h] | Catalyst mass [g] | Fraction of light phase of total liquid product [%] | Conversion of reactant* [%] | Water [g/100 g] | n-Butanol [g/100 g] | n-Hexanol [g/100 g] | 2-Ethyl-pentanol [g/100 g] |
|---|---|---|---|---|---|---|---|---|---|---|---|---|
| 1 | n-Hexanol | 340 | 0 | 2.7 | 8.2 | 30.1 | 88.9 | 91.7 | 1.7 | | 8.3 | 0.7 |
| 2 | n-Hexanol | 320 | 0 | 1.8 | 5.5 | 30.1 | 93.6 | 71.7 | 1.9 | | 28.3 | 0.5 |
| 3 | n-Hexanol | 340 | 0 | 1.8 | 5.5 | 30.1 | 86.4 | 88.5 | 0.6 | | 11.5 | 0.6 |
| 4 | n-Hexanol | 300 | 0 | 1.8 | 5.5 | 30.1 | 100.0 | 42.2 | 3.6 | | 57.8 | 0.2 |
| 5 | n-Hexanol | 320 | 0 | 2.7 | 8.2 | 30.1 | 100.0 | 48.5 | 3.8 | | 51.5 | 0.2 |

TABLE 1-continued

Self-condensation of n-hexanol

| | | | | | | | | | | | |
|---|---|---|---|---|---|---|---|---|---|---|---|
| 6** | n-Hexanol | 300 | 60 | 10.7 | 60.0 | 52.2 | 100.0 | 7.5 | 2.5 | | 92.5 |
| 7 | n-Hexanol | 330 | 5 | 3.9 | 21.6 | 53.2 | 100.0 | 20.9 | 2.4 | 2.1 | 79.1 |

| Number | 2-Butyl-octanol [g/100 g] | Hexanal [g/100 g] | 2-Butyl-octanal [g/100 g] | Pentane [g/100 g] | Hexane [g/100 g] | 1-Hexene [g/100 g] | Undecane [g/100 g] | 5-Methyl-undecane [g/100 g] | Sum of further alkanes [g/100 g] | Sum of further alkenes [g/100 g] | Sum of alkanes >C9 [g/100 g] | Sum of alkanes >C9 [g/100 g] |
|---|---|---|---|---|---|---|---|---|---|---|---|---|
| 1 | 2.9 | 6.4 | 5.2 | 2.0 | 7.5 | 0.7 | 22.1 | 15.8 | 1.9 | | 9.4 | 39.7 | 9.4 |
| 2 | 9.5 | 11.6 | 7.8 | 0.6 | 5.4 | 0.4 | 7.5 | 11.2 | 4.0 | | 5.8 | 22.7 | 5.8 |
| 3 | 2.9 | 6.7 | 5.0 | 1.0 | 6.1 | 0.5 | 19.3 | 16.6 | 2.1 | | 9.4 | 37.9 | 9.4 |
| 4 | 11.4 | 9.6 | 3.7 | 0.2 | 3.5 | 0.3 | 1.0 | 3.4 | 0.3 | | 2.3 | 4.7 | 2.3 |
| 5 | 8.6 | 12.8 | 4.1 | 0.5 | 5.8 | 0.5 | 1.6 | 4.5 | 0.4 | | 2.7 | 6.6 | 2.7 |
| 6** | 3.1 | | 0.2 | | | | 0.3 | | | | 1.4 | 0.3 | 1.4 |
| 7 | 2.7 | 5.0 | 1.0 | | | | 1.0 | 1.7 | | | 3.6 | 2.7 | 3.3 |

*Calculated calibrated substance
**Experiment in the liquid phase

TABLE 2

Reaction of n-hexanol with alcohols and ketones

| Number | Reactant 1 | Reactant 2 | Molar ratio | Reactor temperature [° C.] | Pressure (relative) [bar] | Catalyst loading [mmol/h · g (Cat)] | Throughput [g/h] | Catalyst mass [g] | Fraction of light phase of total liquid product [%] |
|---|---|---|---|---|---|---|---|---|---|
| 8 | 2-Propanol | n-Hexanol | 1:2 | 330 | 0 | 3.72 | 17.1 | 52.2 | 76.8 |
| 9 | 2-Propanol | n-Hexanol | 1:2 | 330 | 10 | 3.72 | 17.1 | 52.2 | 93.6 |
| 10 | Acetone | n-Hexanol | 1:2 | 345 | 0 | 3.89 | 18.6 | 54.7 | 96.0 |
| 11 | Acetone | n-Hexanol | 1:2 | 345 | 20 | 3.89 | 18.6 | 54.7 | 93.1 |
| 12 | Acetone | n-Hexanol | 1:2 | 330 | 0 | 3.89 | 18.6 | 54.7 | 98.0 |

| Number | Conversion rate reactant 1/reactant 2 [%] | Water [g/100 g] | n-Hexanol [%] | 2-Butyloctanol [%] | Hexanal [%] | 2-Butyloctanal [%] | Hexane [%] | Undecane [%] | 2-Propanone [%] |
|---|---|---|---|---|---|---|---|---|---|
| 8 | 100**/44.7* | 3.5 | 41.0 | 2.1 | 2.7 | | | | 2.5 |
| 9 | 100**/52.8* | 3.0 | 28.9 | 2.8 | | | | | 0.9 |
| 10 | 94.4**/93.2* | 0.5 | 4.6 | 1.2 | 1.0 | 1.2 | 9.2 | | 0.7 |
| 11 | 91.0**/62.3* | 2.0 | 28.6 | 2.5 | 1.6 | 0.7 | 9.5 | 3.1 | 1.1 |
| 12 | 90.3**/52.9* | 2.4 | 26.2 | 4.0 | 3.3 | 1.6 | 2.1 | 0.3 | 1.2 |

| Number | 2-Nonanone [%] | 2-Nonanole [%] | 8-Pentadecanone [%] | 8-Pentadecanol [%] | Pentadecane [%] | Sum of further alkanes [%] | Sum of further alkenes [%] | Sum of alkanes >C9 [%] | Sum of alkenes >C9 [%] |
|---|---|---|---|---|---|---|---|---|---|
| 8 | 7.1 | 4.5 | 17.8 | 6.1 | 4.6 | 0.2 | | 4.7 | |
| 9 | 5.4 | 7.2 | 20.8 | 12.6 | 4.9 | 1.0 | 2.5 | 5.8 | 0.2 |
| 10 | 6.2 | 0.7 | 42.4 | 1.7 | 0.9 | 2.0 | 2.8 | 2.8 | 2.8 |
| 11 | 6.8 | 2.5 | 13.9 | 1.7 | 1.8 | 5.5 | 3.4 | 10.5 | 3.4 |
| 12 | 8.8 | 2.5 | 21.8 | 2.8 | 1.8 | 2.0 | 0.6 | 2.3 | 0.6 |

*Calculated calibrated substance
**Calculated by means of MS peak area

TABLE 3

Reactions of n-butanol and effect of water on product selectivity

| Number | Reactant 1 | Reactant 2 | Molar ratio | Reactor temperature [° C.] | Pressure (relative) [bar] | Catalyst loading [mmol/h · g (Cat)] | Through-put [g/h] | Catalyst mass [g] | Fraction of light phase of total liquid product [%] | Conversion rate reactant 1/reactant 2 [%] | Water (formed) [g/100 g] | n-Butanol [%] |
|---|---|---|---|---|---|---|---|---|---|---|---|---|
| 13 | n-Butanol[1] | — | | 330 | 0 | 3.66 | 7.1 | 28.4 | 93.7 | 73.5* | 2.7 | 18.0 |
| 14 | n-Butanol[2] | — | | 330 | 0 | 3.85 | 7.3 | 28.4 | 93.4 | 76.9* | 2.0 | 21.8 |
| 15 | n-Butanol[3] | — | | 330 | 0 | 2.12 | 5.1 | 52.2 | 94.4 | 56.9* | 2.5 | 24.9 |
| 16 | n-Butanol[3] | — | | 330 | 10 | 2.12 | 5.1 | 52.2 | 76.8 | 48.8* | 2.8 | 29.5 |
| 17 | n-Butanol | — | | 330 | 0 | 3.64 | 8.0 | 29.8 | 100.0 | 28.9* | 3.5 | 60.8 |

TABLE 3-continued

Reactions of n-butanol and effect of water on product selectivity

| 18 | n-Butanol | — | | 345 | 0 | 3.64 | 8.0 | 29.8 | 100.0 | 39.4* | 4.4 | 53.6 |
| 19 | n-Butanol | Butanal | 2:1 | 330 | 10 | 3.87 | 15.1 | 53.2 | 92.9 | 55.2*/87.4* | 3.7 | 36.6 |
| 20 | n-Butanol | Acetaldehyde | 1:1 | 340 | 0 | 3.56 | 6.3 | 29.8 | 62.5 | 74.7*/99.2* | 2.8 | 19.2 |

| Number | 2-Ethyl-butanol [%] | 2-Ethyl-butanal [%] | 1 Hexanal [%] | 2-Ethyl-hexanol [%] | 3-Methyl-heptane [%] | Butanol [%] | 2-Ethyl-hexanal [%] | Heptane [%] | Sum of further alkanes [%] | Sum of further alkenes [%] | Sum of alkanes >C9 [%] | Sum of alkenes >C9 [%] |
|---|---|---|---|---|---|---|---|---|---|---|---|---|
| 13 | | | | 21.3 | 11.1 | 7.3 | 14.7 | 7.5 | 1.2 | 2.4 | 1.2 | 2.0 |
| 14 | | | | 27.9 | 7.5 | 6.8 | 14.5 | 5.7 | 5.7 | 1.7 | 5.7 | |
| 15 | | | | 27.7 | 3.7 | 8.1 | 17.2 | 3.0 | 0.3 | 2.0 | 0.3 | |
| 16 | | | | 29.3 | 7.3 | 5.3 | 10.5 | 4.9 | 4.1 | 0.4 | 4.1 | |
| 17 | | | | 13.9 | 2.1 | 12.2 | 4.6 | | | 0.6 | | |
| 18 | | | | 12.4 | 3.6 | 14.7 | 6.6 | | | 0.9 | | |
| 19 | | | | 16.6 | 7.0 | 3.8 | 11.6 | | 0.9 | 6.3 | 0.5 | 1.4 |
| 20 | 3.5 | 3.5 | 3.5 | 6.3 | | 10.9 | 12.1 | 5.9 | 5.0 | 1.5 | 3.1 | 1.5 |

*Calculated calibrated substance
[1] Butanol-water mixture having 90 mol % butanol
[2] Butanol-water mixture having 80 mol % butanol
[3] Butanol-water mixture having 50 mol % butanol

TABLE 4

Calibrated values from experiments 8 to 20

| | Number | | | | | | | | | | | | |
|---|---|---|---|---|---|---|---|---|---|---|---|---|---|
| | 8 | 9 | 10 | 11 | 12 | 13 | 14 | 15 | 16 | 17 | 18 | 19 | 20 |
| n-Butanol [g/100 g] | | | | | | 25.8 | 32.4 | 34.7 | 41.2 | 71.1 | 60.7 | 36.6 | 19.2 |
| n-Butanol [%] | | | | | | 18.0 | 21.8 | 24.9 | 29.5 | 60.8 | 53.6 | 30.0 | 15.9 |
| n-Hexanol [g/100 g] | 42.7 | 36.5 | 4.1 | 22.7 | 28.5 | | | | | | | | |
| n-Hexanol [%] | 41.0 | 28.9 | 4.6 | 28.6 | 26.2 | | | | | | | | |
| 2-Ethylhexanol [g/100 g] | | | | | | 12.9 | 17.3 | 15.3 | 16.6 | 5.4 | 4.8 | | |
| 2-Ethylhexanol [%] | | | | | | 21.3 | 27.9 | 27.7 | 29.3 | 13.9 | 12.4 | | |
| Butanal [g/100 g] | | | | | | 10.5 | 10.0 | 11.6 | 5.6 | 13.7 | 17.5 | | |
| Butanal [%] | | | | | | 7.3 | 6.8 | 8.1 | 5.3 | 12.2 | 14.7 | | |
| Hexanal [g/100 g] | 2.7 | | | 1.1 | | | | | | | | | |
| Hexanal [%] | 2.7 | | | 1.6 | | | | | | | | | |
| 3-Methylheptane [g/100 g] | | | | | | 5.6 | 3.4 | | 2.8 | | | | |
| 3-Methylheptane [%] | | | | | | 11.1 | 7.5 | | 7.3 | | | | |

All of the values reported in Tables 1 to 4 relate to the light phase which usually makes up at least 92% by weight of the sample in the experiments carried out. The heavy phase consists of more than 90% by weight water and was not further analyzed.

In Tables 2 and 3 the values relate to area percent, i.e. to the fraction of the peak area of the relevant peak in a ratio to the sum of all of the automatically identified peaks of the chromatogram. The detector used was a mass spectrometer.

The corresponding calibrated values which were determined by comparison with the respective pure substance for experiments 8 to 20 are shown in Table 4.

In a further experiment (experiment 21) using the above-described apparatus, the coupling or condensation of products of the ABE fermentation was studied. In the ABE fermentation, fermentation produces product mixtures which contain, in particular, acetone, butanol and ethanol in the molar ratio of about 3:6:1 in the aqueous medium. Such ABE fermentation products having the corresponding fractions of acetone, butanol and ethanol are available commercially for example.

In the context of studies carried out, however, no fermentation products were used, but mixtures of the individual substances. The molar ratios of the reactant mixture in the present case were acetone:butanol:ethanol (A:B:E) 3:6:1. These molar reactant ratios result in experiment 21a (light product phase) and 21b (heavy product phase) from the customary product composition of the ABE fermentation.

In addition, 10 percent by mass water were added, since an aqueous solution is formed in the ABE fermentation.

The results of these experiments are summarized in the following Table 5. In contrast to the experiments displayed in Tables 1 to 4, in experiment 21, both the light phase and the heavy phase were analyzed.

The formation of the main products of the condensation of the ABE fermentation products is made clear with reference to the following equations, wherein hexanol (HexOH) is formed by condensation of butanol (BuOH) and ethanol (EtOH):

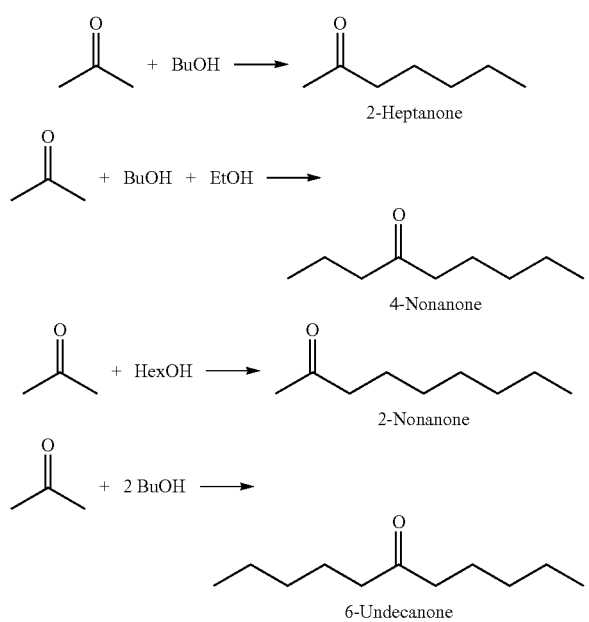

TABLE 5

Condensation of a synthetic ABE-water mixture
(ABE = acetone-butanol-ethanol in the molar ratio A:B:E of 3:6:1)

| Number | Phase | Reactant 1 | Reactant 2 | Reactant 3 | Reactant 4 | Molar ratio | Reactor temperature [° C.] [° C.] | Pressure (relative) [bar] | Catalyst loading [mmol/ h · g (Cat)] | Throughput [g/h] |
|---|---|---|---|---|---|---|---|---|---|---|
| 21a | light | Acetone | n-Butanol | Ethanol | 10% by weight water | 3:6:1 | 345 | 0 | 6.60 | 12.9 |
| 21b | heavy | Acetone | n-Butanol | Ethanol | 10% by weight water | 3:6:1 | 345 | 0 | 6.60 | 12.9 |

| Number | Catalyst mass [g] | Fraction of total liquid product [%] | Water [g/100 g] | n-Butanol [%] | Butanal [%] | n-Hexanol [%] | 2-Ethyl-hexanol [%] | 2-Ethyl-butanol [%] | 2-Pro-panone [%] | Heptanone [%] |
|---|---|---|---|---|---|---|---|---|---|---|
| 21a | 29.8 | 77.6 | 2.3 | 11.4 | 2.1 | 0.7 | 3.0 | 0.5 | 2.1 | 10.1 |
| 21b | 29.8 | 28.3 | 84.6 | 19.9 | 2.0 |  | 1.3 |  |  | 4.8 |

| Number | 2-Heptanol [%] | 4-Nonanone [%] | 2-Nonanone [%] | 6-Undecanone [%] | 6-Undecanol [%] | Pentane [%] | Heptane [%] | Total [%] |
|---|---|---|---|---|---|---|---|---|
| 21a | 1.6 | 3.5 | 0.6 | 22.2 | 2.1 | 1.9 | 1.8 | 63.5 |
| 21b |  | 1.6 |  | 11.7 | 0.9 |  |  | 42.0 |

The invention claimed is:

1. A method for the catalytic condensation or coupling of an organic compound containing at least one of an oxo and a hydroxyl function with a CH-acidic compound for the purpose of generating higher alcohols, aldehydes, ketones, aromatics and alkanes and mixtures thereof,
wherein the method comprises the following step:
(A) at least one organic compound containing at least one of an oxo and a hydroxyl function and which has at least 3 carbon atoms and is selected from the group consisting of primary and secondary alcohols, aldehydes and ketones and mixtures thereof,
is reacted with
(B) with at least one CH-acidic compound which has at least 3 carbon atoms,
in the presence of at least one catalyst,
wherein the catalyst comprises an activated carbon substrate that is provided with at least one metal,
wherein the catalyst has at least one monovalent metal $M^I$ in the form of an alkali metal and at least one divalent metal $M^{II}$ the form calcium and/or magnesium, and
wherein the catalyst contains phosphorus in the form of phosphates,
wherein the following molar ratios apply:
(i) $0.5 \leq M^I/M^{II} \leq 5$;
(ii) $2 \leq M^{II}/P \leq 30$; and
(iii) $1 \leq M^I/P \leq 60$.

2. The method as claimed in claim 1, wherein the organic compound (A) containing at least one of an oxo and a hydroxyl function is selected from $C_3$-$C_{25}$ compounds and mixtures of various compounds having these carbon numbers.

3. The method as claimed in claim 1, wherein the CH-acidic compound (B) is selected from $C_3$-$C_{25}$ compounds and mixtures of various compounds having these carbon numbers.

4. The method as claimed in claim 1, wherein the CH-acidic compound (B) is selected from the group consisting of primary and secondary alcohols, carboxylic acids, carboxylic anhydrides, carboxylic esters, aldehydes, ketones, nitriles, nitro compounds, organic nitrates and mixtures thereof.

5. The method as claimed in claim 1, wherein the CH-acidic compound (B) has at least one acidic hydrogen atom on a carbon atom in the vicinal or alpha-position to at least one carbon atom having at least one electron-withdrawing group or has at least one acidic hydrogen atom on a carbon atom in the geminal position to an electron-withdrawing group.

6. The method as claimed in claim 1, wherein the CH-acidic compound (B) is selected from primary and secondary alcohols of the general formula (I)

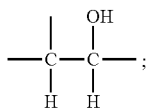
(I)

nitro compounds and/or organic nitrates of the general formula (II)

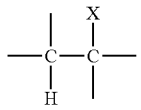
(II)

where X=NO₂, ONO₂;
carbonyl compounds of the general formula (III)

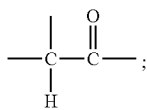
(III)

nitrile compounds of the general formula (IV)

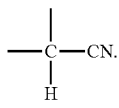
(IV)

7. The method as claimed in claim 1, wherein a further compound selected from the group consisting of lower alcohols and water is added to the reactants.

8. The method as claimed in claim 1, wherein the organic compound (A) and the CH-acidic compound (B) are identical.

9. The method as claimed in claim 1, wherein the method is carried out in the gas phase, in the liquid phase or in the supercritical state.

10. The method as claimed in claim 1, wherein the method is carried out in the gas phase.

11. The method as claimed in claim 1, wherein the method is carried out at temperatures in the range from 150° C. to 600° C.

12. The method as claimed in claim 1, wherein is carried out at reduced pressure, at atmospheric pressure or at elevated pressure.

13. The method as claimed in claim 1, wherein the method is carried out at a pressure in the range from atmospheric pressure to 150 bar.

14. The method as claimed in claim 1, wherein the method is carried out in the presence of water and/or in the presence of hydrogen.

15. The method as claimed in claim 1, wherein the method is carried out with a space/time-yield, reported as amount of all products formed per volume of catalyst and per unit time, in the range from 10 to 3,000 g/(liter·h), and
wherein the method is carried out at a space velocity, reported as amount of substance of all products formed per mass of catalyst and per unit time, in the range from 0.1 to 100 mol/(kg·h), and
wherein the method is carried out with a conversion rate based on amount of substance, based on the reactants used, in the range from 15 to 100%.

16. The method as claimed in claim 1, wherein the catalyst and/or the activated carbon substrate is formed so as to be basic.

17. The method as claimed in claim 16, wherein the basic form is provided by at least one of the following compounds: (i) hydroxides; (ii) oxides; (iii) salts of inorganic acids based on phosphates, sulfates, carbonates and nitrates; (iv) salts of organic acids based on lactates, phthalates, formates and acetates; and (v) alcoholates.

18. The method as claimed in claim 1, wherein the catalyst and/or the activated carbon substrate has a specific surface area (BET) in the range from 450 to 3,000 m²/g and a micropore volume according to Gurvich in the range from 0.1 to 3.0 ml/g.

19. The method as claimed in claim 1, wherein the resultant product or product mixture is finally subjected to a hydrogenation process step or to a hydrotreating process step.

20. A method for the catalytic condensation or coupling of an organic compound containing at least one of an oxo and a hydroxyl function with a CH-acidic compound for generating higher alcohols, aldehydes, ketones, alkanes and mixtures thereof,
wherein the method comprises the step of using an activated carbon substrate provided with at least one metal as a catalyst,
wherein the catalyst has at least one monovalent metal $M^I$ in the form of an alkali metal and at least one divalent metal $M^{II}$ in the form calcium and/or magnesium, and wherein the catalyst contains phosphorus in the form of phosphates,
wherein the following molar ratios apply:
(i) $0.5 \leq M^I/M^{II} \leq 5$;
(ii) $2 \leq M^{II}/P \leq 30$; and
(iii) $1 \leq M^I/P \leq 60$.

* * * * *